US006710328B1

(12) United States Patent
Mastro et al.

(10) Patent No.: US 6,710,328 B1
(45) Date of Patent: Mar. 23, 2004

(54) FIBER OPTIC COMPOSITE DAMAGE SENSOR

(75) Inventors: Stephen A. Mastro, Glen Mills, PA (US); Veerendra K. Mathur, Beltsville, MD (US); Andrew W. Jarrett, Ellicott City, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 100 days.

(21) Appl. No.: 10/083,521

(22) Filed: Feb. 27, 2002

(51) Int. Cl.[7] .............. G01J 1/42; G01L 1/24; G01L 3/02; G01B 11/16
(52) U.S. Cl. .............. 250/227.14; 250/227.11; 250/227.18; 73/800; 73/862.324; 73/862.624; 356/32
(58) Field of Search .............. 250/227.14, 227.11, 250/227.18, 227.15, 227.16, 221; 356/32; 73/800, 862.324, 862.624

(56) References Cited

U.S. PATENT DOCUMENTS

| | | | |
|---|---|---|---|
| 4,020,765 A | | 5/1977 | Glass et al. |
| 4,372,211 A | | 2/1983 | Dante |
| 4,473,747 A | * | 9/1984 | Brogardh |
| 4,772,417 A | | 9/1988 | Pappalardo et al. |
| 4,991,150 A | * | 2/1991 | Wixom |
| 5,446,334 A | * | 8/1995 | Gaffney |
| 5,581,082 A | | 12/1996 | Hansma et al. |
| 5,905,260 A | * | 5/1999 | Sage |
| 6,071,632 A | | 6/2000 | Hall-Goulle |
| 6,117,574 A | | 9/2000 | Watanabe et al. |
| 6,159,394 A | | 12/2000 | Akiyama et al. |
| 6,270,117 B1 | * | 8/2001 | Storey |
| 6,281,617 B1 | | 8/2001 | Qiu et al. |
| 6,420,724 B1 | * | 7/2002 | Struye |
| 6,581,474 B2 | * | 6/2003 | Goods |
| 2001/0054857 A1 | | 12/2001 | Qui et al. |

OTHER PUBLICATIONS

"DERA Propose Triboluminescent Damage Sensors," Aug. 27, 1999, Institute of Physics Website (http://www.iop.org) at http://www.iop.org/Physics/News/0154j (1 page).

I. Sage, R. Badcook, L. Humberstone, N. Geddes, M. Kemp and G. Bourhill, "Triboluminescent Damage Sensors," *Smart Materials and Structures*, vol. 8, No. 4, pp. 504–510 (Aug. 1999); electronic copy available from Institute of Physics Website (http://www.iop.org) at http://www.iop.org/EJ/S/1/N91002209/journal/0964–1726 (electronic copy, 7 pages, provided herewith).

* cited by examiner

*Primary Examiner*—David Porta
*Assistant Examiner*—David C Meyer
(74) *Attorney, Agent, or Firm*—Howard Kaiser

(57) ABSTRACT

A composite structure contains crystalline and/or polycrystalline triboluminescent elements distributed therein externally and/or internally, totally and/or regionally. The structure is instrumented with at least one optical fiber which is coupled therewith penetratingly and/or superficially/tangentially. Each optical fiber is exteriorly light transparent/translucent along at least a longitudinal portion thereof which is situate in the vicinity of at least one triboluminescent element. Concomitant with the occurrence of damage in and/or on the structure is the occurrence of mechanical action with respect to at least one triboluminescent element, a consequence of which is the occurrence of triboluminescence which, to at least some degree, passes radially into at least one optical fiber so as to reach the optical fiber's transmissive axial core and thereby be transmitted to remotely located photosensitive equipment. The triboluminescent elements can exist wholly and/or partly in various capacities, e.g., as fiber reinforcement and/or particle reinforcement and/or particle filler.

19 Claims, 9 Drawing Sheets

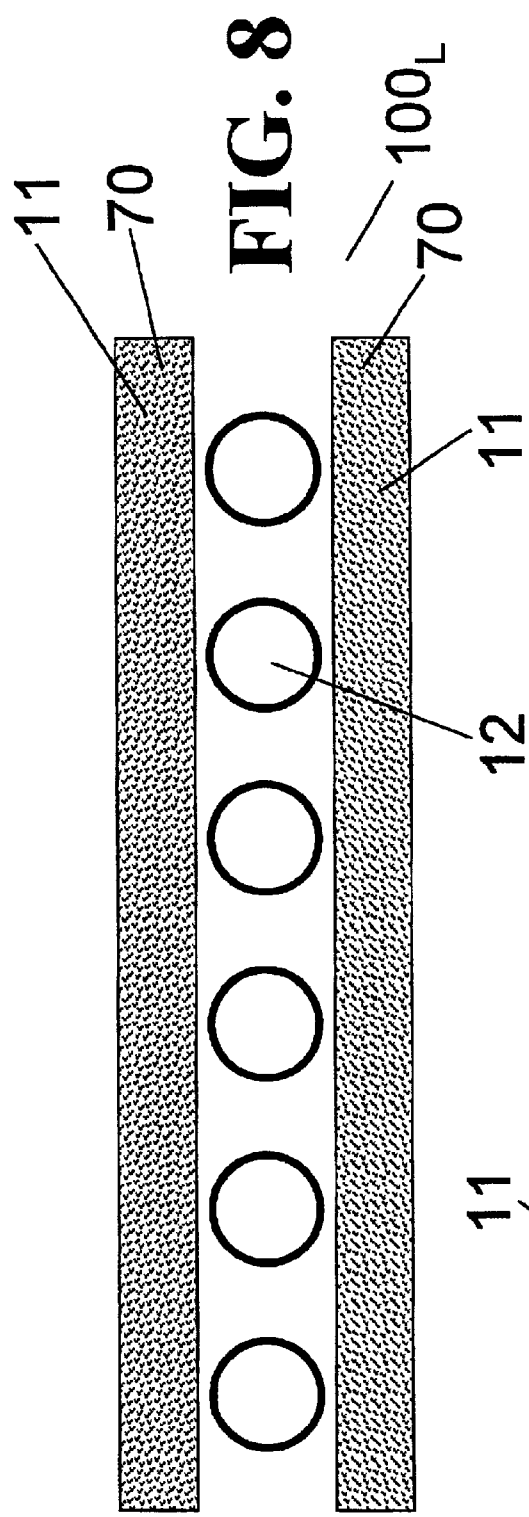
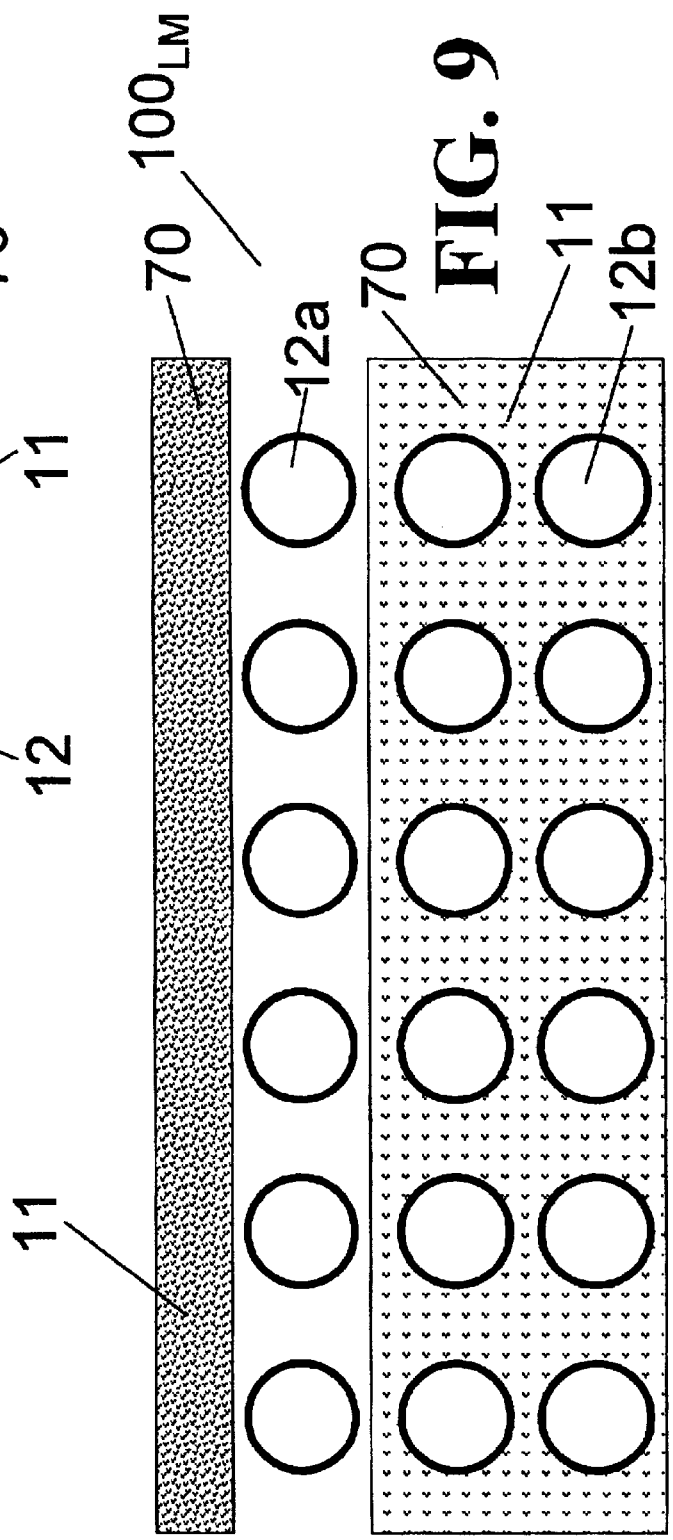

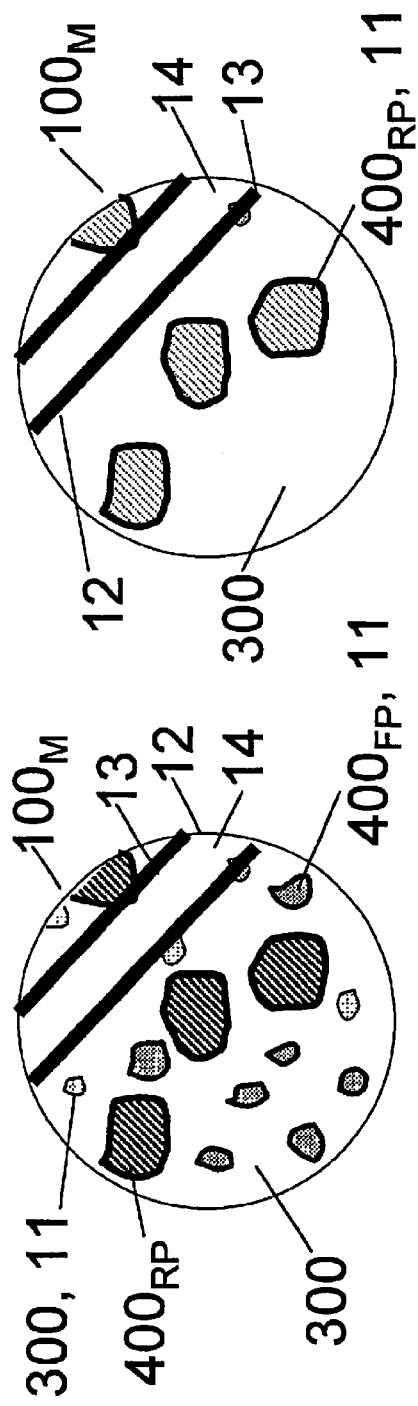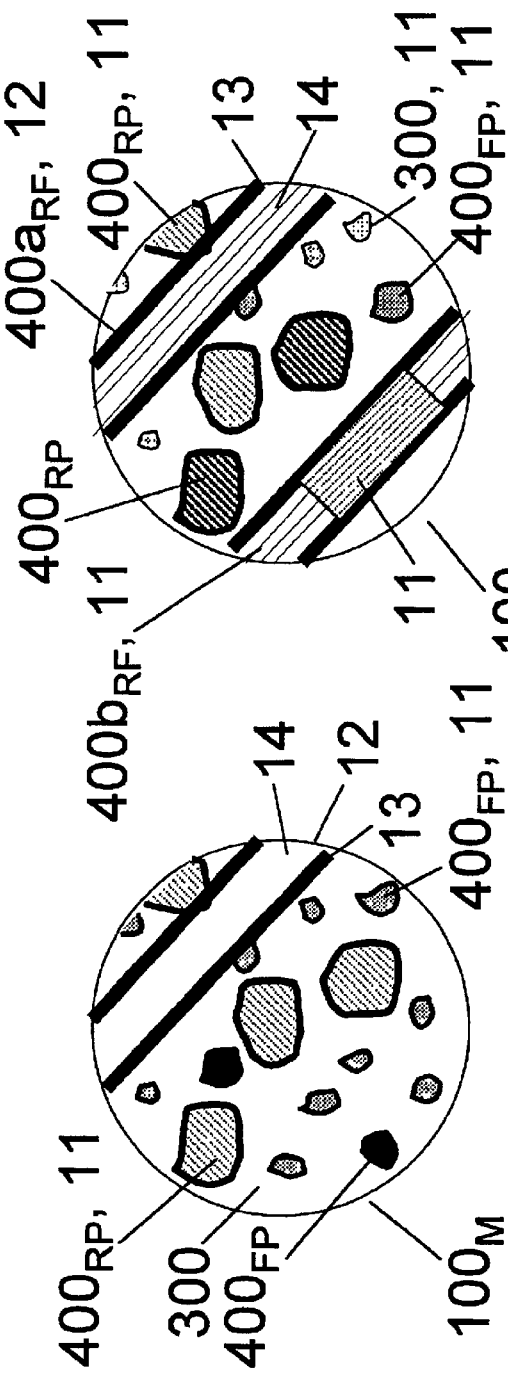

FIBER OPTIC COMPOSITE DAMAGE SENSOR

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to methods and apparatuses for sensing or detecting structural damage in objects, more particularly to methods and apparatuses for sensing or detecting fractures, delamination and other forms of mechanical damage in structures such as composites.

Presently there is no completely satisfactory method or mature sensing technology to detect composite damage in-situ and in real-time, or to remotely interrogate such occurrences. Sage et al. U.S. Pat. No. 5,905,260 issued May 18, 1999, incorporated herein by reference, disclose a sensing technology to make such measurements; however, the technology disclosed by Sage et al. has its limitations. The sensor proposed by Sage et al. is a discrete sensor (described by Sage et al. as including "a small piece of a triboluminescent material") that will locate damage only when damage occurs within the sensor's triboluminescent material itself. This approach by Sage et al. is problematic for various reasons. Firstly, the area (areas) of interest is (are) very specifically targeted according to the Sage et al. methodology, which assumes that the user of the composite structure knows exactly where damage will occur. Secondly, the Sage et al. methodology assumes that any damage in the composite is transferred to cracking in the sensor's triboluminescent material. Thirdly, measurements made at or near the outside surface of the composite may be impossible to make in accordance with the Sage et al. methodology.

In addition to Sage et al., other United States patents disclose triboluminescence or triboluminescent material in some context or capacity, including the following which are incorporated herein by reference: Qiu et al. U.S. Pat. No. 6,281,617 B1 issued Aug. 18, 2001; Storey U.S. Pat. No. 6,270,117 B1 issued Aug. 7, 2001, Akiyama et al. U.S. Pat. No. 6,159,394 issued Dec. 12, 2000; Watanabe et al. U.S. Pat. No. 6,117,574 issued Sep. 12, 2000; Hall-Goulle U.S. Pat. No. 6,071,632 issued Jun. 6, 2000; Hansma et al. U.S. Pat. No. 5,581,082 issued Dec. 3, 1996; Pappalardo et al. U.S. Pat. No. 4,772,417 issued Sep. 20, 1988; Dante U.S. Pat. No. 4,372,211 issued Feb. 8, 1983; Glass, deceased et al. U.S. Pat. No. 4,020,765 issued May 3, 1977.

"Triboluminescent" (sometimes called "mechanoluminescent") material is a substance (usually, a crystalline substance) that, when fractured or otherwise subjected to some form of mechanical action, releases optical radiation in the visible spectrum (about 400–700 nm). Although the consistency of some triboluminescent materials may be roughly compared to that of sand, this is not a valid comparison for many triboluminescent materials. There are numerous different triboluminescent substances which share certain attributes and thus exhibit triboluminescent properties. A triboluminescent substance can be comprised of any of various organic and inorganic materials. As used herein, the terms triboluminescence (or triboluminescent) and mechanoluminescence (or mechanoluminescent) are synonymous. Both terms refer to luminescence (light emission) resulting from mechanical action, such as friction (rubbing), pressure, fracturing, scratching, striking, sawing, crushing, pulverizing, smashing or tearing.

Derivationally, triboluminescence comes from "tribo" or the Greek term "tribein," meaning "friction" or "rubbing." Notwithstanding that the prefix "tribo" seems to connote a more specific meaning of "friction" or "rubbing," the terms triboluminescence and triboluminescent are intended herein to denote luminescence resulting from any and all forms of mechanical action. The prefix "mechano" in "mechanoluminescence" and "mechanoluminescent" seems to have a broader connotation more in keeping with the broadest concept of luminescence resulting from any and all forms of mechanical action. Nevertheless, the terms triboluminescence and mechanoluminescence are used fairly interchangeably in conventional usage. Thus, the terms triboluminescence and mechanoluminescence are intended herein to have the same broadest meaning, viz., luminescence resulting from any and all forms of mechanical action. Consistent with conventional usage, the terms fractoluminescence and fractoluminescent are intended herein to more specifically denote luminescence resulting from fracturing, since the prefix "fracto" suggests the more specific meaning of "fracture."

SUMMARY OF THE INVENTION

In view of the foregoing, it is an object of the present invention to provide method and apparatus for remotely detecting mechanical damage (e.g., fracture or delamination) occurring in a structure of any kind, especially to provide such method and apparatus in relation to a structure which is a composite structure such as a matrix composite or a laminar composite.

It is another object of the present invention to provide method and apparatus for remotely monitoring the mechanical damage condition of a structure which is known to be susceptible to certain types of damage such as involving fracture or delamination.

In accordance with typical practice of the present invention, a combination is provided which is suitable for detecting damage in an object. The combination comprises fiber optic means and triboluminescent means. The fiber optic means and the triboluminescent means are each adaptable to association with the object so that a mechanical event attendant the damage is capable of causing the triboluminescent means to emit light at least some of which is transmissible by the fiber optic means.

According to many embodiments of the present invention, "damage-autosensitive" apparatus (e.g., apparatus which, in functional effect, is capable of automatically sensing damage to itself) is provided. The damage-autosensitive apparatus comprises a structure, at least one fiber optic line, and at least one triboluminescent element. Each fiber optic line is connectable to a photodetector and is situated so that a portion of the fiber optic line is in communication with the structure. Each triboluminescent element is integrated with the structure and is sufficiently proximate a fiber optic line so that, upon an occurrence of damage to the structure: (i) an accompanying mechanical action upon the triboluminescent element results in a luminescent emission of light by the triboluminescent element; and, (ii) at least a portion of the luminescently emitted light is transmissible to the photodetector via the fiber optic line.

According to frequent inventive practice, a method for sensing mechanical damage comprises triboluminescently radiating light in response to the damage, and fiber optically conveying at least some of the triboluminescently radiated light so as be informative about the mechanical damage.

Many inventive embodiments provide a method of sensing the damage condition of an object. The method comprises (a) integrating triboluminescent material with the object, and (b) associating at least one fiber optic line with the object and with a photosensitive device. The at least one fiber optic line is associated with the object and with a photosensitive device so that, following a damage-causing event accompanied by a mechanical action upon at least some of the integrated triboluminescent material, a quantity of a resultant triboluminescent light emanation is transmitted by at least one fiber optic line to the photosensitive device.

Featured by typical embodiments of the present invention is a sequence of events including a damage-related mechanical action with respect to triboluminescent material, followed by a triboluminescent emission of light, followed by a fiber optic admission of at least some of the emitted light, followed by a fiber optic transmission of at least some of the admitted light, followed by an electronic indication (e.g., including an identification, a registration, a recordation, a representation, a readout, a signal, a digitization, a processing and/or a display) of at least some of the transmitted light.

According to many inventive embodiments, the present invention's fiber optic sensor senses fracture, delamination or similar mechanical damage in composites. The composite structure is doped with triboluminescent crystals, which release light upon fracture. The optical fiber then detects the light along its length, and transmits the light to a photodetector—thereby indicating mechanical damage to the composite structure. The present invention thus affords a methodology for monitoring the physical condition of composite and other structures.

According to many embodiments of the present invention, a distributed fiber optic composite damage sensor utilizes triboluminescent material and optical fiber to detect mechanical damage (such as cracking or delamination) in a composite, and to transmit this information to a remote location. An important premise of typical embodiments of the present invention is that an optical fiber (sometimes referred to as an optical thread, line, fiber, filament or strand) can be embedded in a composite structure, and—anywhere along the optical fiber's length—detect damage occurring within the composite structure, wherein the composite structure has been impregnated (e.g., in its matrix phase) with triboluminescent crystals. The present invention can be applied to any composite structure, including but not limited to edifices and other main structures, support structures, piping, propellers, hull sections and machinery components. The present invention can also be applied to non-composite structures meeting these and other descriptions.

The present invention admits of application to any structure which permits the association therewith (e.g., embedment therein) of a fiber optic line. The present invention is especially suitable for application to composite structures. The term "fiber optic line," as used herein, refers to any discrete fiber optic member, such as an optical fiber, optical thread, optical filament, optical strand or a pluralized form thereof such as represented by a fiber optic cable. In accordance with the present invention, the association of a fiber optic line can be accomplished in any of several ways, such as by means of insertion of the fiber optic line after the structure has been made (for example, by machining the structure and adhesively bonding the fiber optic line in place), or by means of molding the fiber optic line into the structure during construction of the structure.

Fiber optic lines in general have certain qualities which are especially suited for inventive practice. They can be made to be relatively small in diameter and weight, yet relatively strong. They are immune to electromagnetic interference (EMI), and can provide distributed or multiplexed measurements. Moreover, fiber optic lines lend themselves to being embedded into rubbers, plastics, composites and even metals. Many inventive embodiments involve composite structures. In inventive application to fiber-reinforced matrix composites, one or more fiber optic lines can each serve as a reinforcement fiber in the fiber-matrix system of the structure.

Incorporated herein by reference are the following United States patents which disclose fiber optic technology: Cohen U.S. Pat. No. 6,080,982 issued Jun 27, 2000; El-Sherif U.S. Pat. No. 5,060,307 issued Oct. 22, 1991; Rode et al U.S. Pat. No. 4,348,665 issued Sep. 7, 1982; Rouam U.S. Pat. No. 4,143,319 issued Mar. 6, 1979; Schutz et al. U.S. Pat. No. 4,509,364 issued Apr. 9, 1985; Jensen U.S. Pat. No. 4,328,462 issued May 4, 1982; Purvis et al. U.S. Pat. No. 4,655,077 issued Apr. 7, 1987; Riegler et al. U.S. Pat. No. 4,092,053 issued May 30, 1978; Slough U.S. Pat. No. 4,107,603 issued Aug. 15, 1978; Considine U.S. Pat. No. 3,981,621 issued Sep. 21, 1976; Fukuyoshi et al. U.S. Pat. No. 5,258,930 issued Nov. 2, 1993; Satake et al. U.S. Pat. No. 4,884,434 issued Dec. 5, 1989; Uejio U.S. Pat. No. 5,015,859 issued May 14, 1991.

Various fiber optic sensor technologies involving structural analysis or wear determination have been known or considered. Fiber optic sensor types which have been embedded for structural analysis include: fiber Bragg grating; long period grating; micro-bend interferometer; Fabry-Periot interferometer. Fiber optic measurement of strain, temperature, pressure, torque, vibration and acoustic fields have all been demonstrated. Structural health monitoring systems employing sacrificial, embedded optical filaments have been proposed for some time, primarily for composite structures. For instance, a fiber optic filament can be embedded into a structure in such a way that, if during its life cycle the loading exceeds the strength at the location of attachment, the optical filament breaks and the excessive load condition can be detected. These and more complex embedded sensor systems are now in use on air and space vehicles and civilian structures. See Udd, Eric, Fiber *Optic Smart Structures*, John Wiley and Sons, Inc., New York, 1995, incorporated herein by reference.

A composite is a combination of two or more materials which differ at the macroscopic level, each different material being a constituent of the composite. The following two references, incorporated herein by reference, are instructive regarding composites: John W. Weeton, Dean M. Peters and Karyn L. Thomas, *Engineers' Guide to Composite Materials*, American Society for Metals, Metals Park, Ohio, 1987 (See, esp., Section 1, entitled "Introduction to Composite Materials"); George Lubin, *Handbook of Composites*, Van Nostrand Reinhold Company, New York, 1982 (See, esp., Chapter 1, entitled "An Overview of Composites").

A matrix composite comprises (i) a filler or reinforcing agent (e.g., fibers, flakes or particles) and (ii) a matrix binder (e.g., a resin). The matrix is the principal phase or aggregate in which the filler or reinforcing agent is embedded or surrounded. Generally, the matrix serves two functions, viz., (i) it holds the reinforcement phase in place, and (ii) under an applied force, it deforms and distributes the stress to the reinforcement constituents. Types of matrix composite materials include metal matrix composite (MMC) materials, ceramic matrix composite (CMC) materials, and polymeric matrix composite (PMC) materials.

Examples of metals (metal elements, or alloys of two or more metal elements) conventionally used as matrices in metal matrix composites are aluminum, titanium, bronze and magnesium. A broad range of fillers or reinforcing agents (e.g., fibers) can be used with lower-melting point matrices in metal matrix composites. For instance, most metals, ceramics and compounds can be used as fillers or reinforcing agents in an aluminum or magnesium matrix. The choice of fillers or reinforcing agents for metal matrix composites becomes increasingly limited as the melting point of the metal matrix material increases.

Ceramic compounds (such as those used as matrices in ceramic matrix composites) are formed by the combination of one or more metallic elements with one or more nonmetallic elements. Examples of ceramic materials include aluminum oxide, magnesium oxide and silica.

There are two main types of polymers, viz., thermoplastics and thermosets. Examples of thermoplastics which can be used as matrix resins include polycarbonate, polyethylene, polystyrene, polypropylene, polyamide, fluoropolymer, thermoplastic polyester, nylon, vinyl, acetal, polycarbonate, polyphenylene oxide, polyetheretherketone (PEEK), polyphenylene sulfide (PPS), polyetherketone ketone (PEKK) and polyetherketone (PEK). Examples of thermosets which can be used as matrix resins include epoxy, polyester, vinyl ester, phenolic, polyimide and bis-maleide.

Conventional types of fillers and reinforcing agents (e.g., reinforcing fibers or particles) used in the fabrication of matrix composites include glass, cotton, aramid, carbon, graphite, polyethylene, boron, steel, polyamide, alumina, silicon carbide and aluminaboria-silica.

A distinction may be drawn between the kinds of constituents in matrix composites which are "reinforcements" and those which are "fillers." The primary function of a "reinforcement" is to be a structural constituent—e.g., to afford strength and/or stiffness. For instance, in a fiber-reinforced plastic composite (FRP), the plastic functions as the matrix, while the fibers function mainly as reinforcements. In contrast, a "filler" is a constituent which is added to a matrix for reasons other than structural (e.g., strength and/or stiffness), such as for increasing electrical conductivity, increasing thermal conductivity, improving fire resistance/retardance, cost reduction, control of shrinkage, increasing volume (e.g., acting as a bulking agent so that less resin is required) or other nonstructural purposes. Typically, fillers are particles that extend rather than reinforce the material. Such systems are generally referred to as "filled" systems. Although the main purpose of fillers is not reinforcement, in some cases the filler may also, to some degree, serve to reinforce the matrix material.

Reinforcements and fillers may come in various forms. Fiber reinforcements are basically fibers, wherein their lengths are significantly greater than their diameters. Fiber reinforced composites have been classified as either "continuous" fiber composites or "discontinuous" fiber composites. Non-fiber reinforcements (and fillers) are characterized by dimensions that are roughly equal along all axes. Non-fiber reinforcements can be spheres, rods, plates, flakes and many other shapes. According to terminology adopted by many, the two categories of matrix reinforcement/filler shapes are (i) fiber and (ii) particle, wherein the term "particle" is synonymous with the term "non-fiber" and refers to any shape other than a fiber shape (which is characterized by length being considerably greater than diameter). The terms "particle" and "non-fiber" are used herein interchangeably to refer to any shape other than a fiber shape.

Generally, fibers are used as reinforcements; however, not all reinforcements are fibers, since particles are also commonly used as reinforcements. Although it is unusual for fibers to serve primarily as fillers, it is much more common for particles to serve primarily as fillers. Generally, matrix-containing constituents which are primarily intended for filler purposes are particles. On the other hand, matrix-containing constituents which are primarily intended for reinforcement purposes may be fibers or particles.

Diverse combinations of matrices along with fillers and/or reinforcements are possible within the basic matrix composite structure. For example, a matrix composite can include, within the same matrix, two or more kinds of reinforcing fibers. Additionally or alternatively, a matrix composite can include, within the same matrix, two or more kinds of reinforcements of various forms among fiber, particle, flake, etc. Additionally or alternatively, a matrix composite can include, within the same matrix, two or more kinds of fillers. Additionally or alternatively, a matrix composite can include, within the same matrix, both reinforcements and fillers. The term "hybrid" has been used to refer to these types of mixed filer and/or reinforcement schemes.

Matrix composites have one or more discontinuous phases surrounded by a three-dimensional continuous phase. There are also various types of non-matrix composites, which lack these attributes. For instance, felts and fabrics have no body matrix, consisting of different kinds of fibers held together by interweaving or entanglement, and perhaps together with a small amount of binder. Laminar composites are not matrix composites, but rather are characterized by flat, layered profiles. Examples of lamanar composites are a sandwich structure, plywood and a metal coated with another metal (e.g., to prevent corrosion). "Sandwich" structures typically have a bulky, lightweight core which is situated between two thin, strong facings.

In accordance with the present invention, the triboluminescent crystals can be integrated with the composite structure in any of various ways or combinations of ways. For instance, according to many embodiments of the present invention, the present invention detects damage occurring within a matrix composite structure which has been impregnated with triboluminescent crystals in the matrix composite's matrix phase. According to some inventive embodiments, the present invention detects damage occurring within a matrix composite which has been impregnated with triboluminescent crystals in its reinforcement phase and/or its filler phase. According to some inventive embodiments, the present invention detects damage occurring within a composite laminate structure which has been impregnated, within its lamina, with triboluminescent crystals.

In inventive practice, triboluminescent elements (e.g., triboluminescent crystals or polycrystals or aggregations thereof) can be integrated with the structure of interest in any of various ways in composites of all kinds, including fiber matrix composites, in particle matrix sit composites, reinforcement-plus-filler hybrid composites, fiber-plus-particle hybrid composites, composite laminates, or combinations thereof. For instance, triboluminescent elements can be, or be included in, some or all of the particle (and/or fiber) reinforcement constituents of a reinforcement-matrix system. Or, triboluminescent elements can be, or be included in, some or all of the particle filler constituents of a filler-matrix system. Or, triboluminescent elements can be, or be included in, some or all of the particle (and/or fiber) reinforcement constituents and/or some or all of the particle filler constituents of a reinforcement-plus-filler-matrix system. Or, triboluminescent elements can be mixed or blended or otherwise combined with the matrix material itself so as to constitute a fully integrated component of such matrix material. The triboluminescent elements can be distributed homogeneously (uniformly) or nonhomogeneously (nonuniformly) within the structure or structural portion with which they are united.

In accordance with the present invention, the triboluminescent elements can be generally distributed (e.g., in homogeneous fashion) at least substantially throughout the structure, or can be more specifically placed in one or more selected locations or zones of interest in the structure. The triboluminescent elements can be situated at or near a surface of the structure, or more deeply inside the structure. A key aspect of inventive practice is that the fiber optic line which is associated with the structure—more particularly, a light-permeable portion of the fiber optic line—be disposed in the vicinity of one or more triboluminescent elements; in other words, a light-permeable fiber optic portion must be positioned sufficiently near a triboluminescent element to permit a sufficient amount of luminescence-generated light to pass through its light-permeable axial exterior (outer covering, e.g., cladding) and reach its axial interior (centrally located optical fiber or fibers) in a sufficient amount or to a sufficient degree that its optical fiber(s) transmit an appreciable amount or degree of light indicative of the luminescence-generated light.

Advantageously, the present invention's fiber optic composite damage sensor affords remote detection of damage on the surface of or within a composite structure or other structure such as a machinery component. The structure of interest can thereby be monitored for damage. The present invention is especially advantageous vis'-a-vis the current state-of-the-art because the present invention: (i) does not presuppose knowledge of the exact location of damage; (i) is a distributed sensor able to detect damage through great lengths; (iii) is a versatile sensor having great flexibility in reaching many areas within a composite or other structure.

Other objects, advantages and features of this invention will become apparent from the following detailed description of the invention when considered in conjunction with the accompanying drawings.

BRIEF DESCRIPTION OF THE DRAWINGS

In order that the present invention may be clearly understood, it will now be described, by way of example, with reference to the accompanying drawings, wherein like numbers indicate the same or similar components, and wherein:

FIG. 8 is a partial elevation view of an embodiment of the present invention, particularly illustrating, similarly as illustrated in FIG. 6, how a composite laminate structure (two lamina shown) can be infiltrated with triboluminescent elements and be coupled with optical fibers (six optical fibers shown in an axial perspective) situated between the lamina.

FIG. 9 is a partial elevation view of an embodiment of the present invention, particularly illustrating how a composite laminate structure can be infiltrated with triboluminescent elements and be coupled with (i) optical fibers (six optical fibers shown in an axial perspective) situated between the lamina, and/or (ii) optical fibers (twelve fibers shown in an axial perspective) situated inside the lamina.

FIG. 10a through FIG. 10d are detailed partial views of various embodiments of the present invention, particularly showing triboluminescent elements and/or particle reinforcements and/or fiber reinforcements and/or optical fibers and the relationships therebetween.

DETAILED DESCRIPTION OF THE INVENTION

Figure 1:
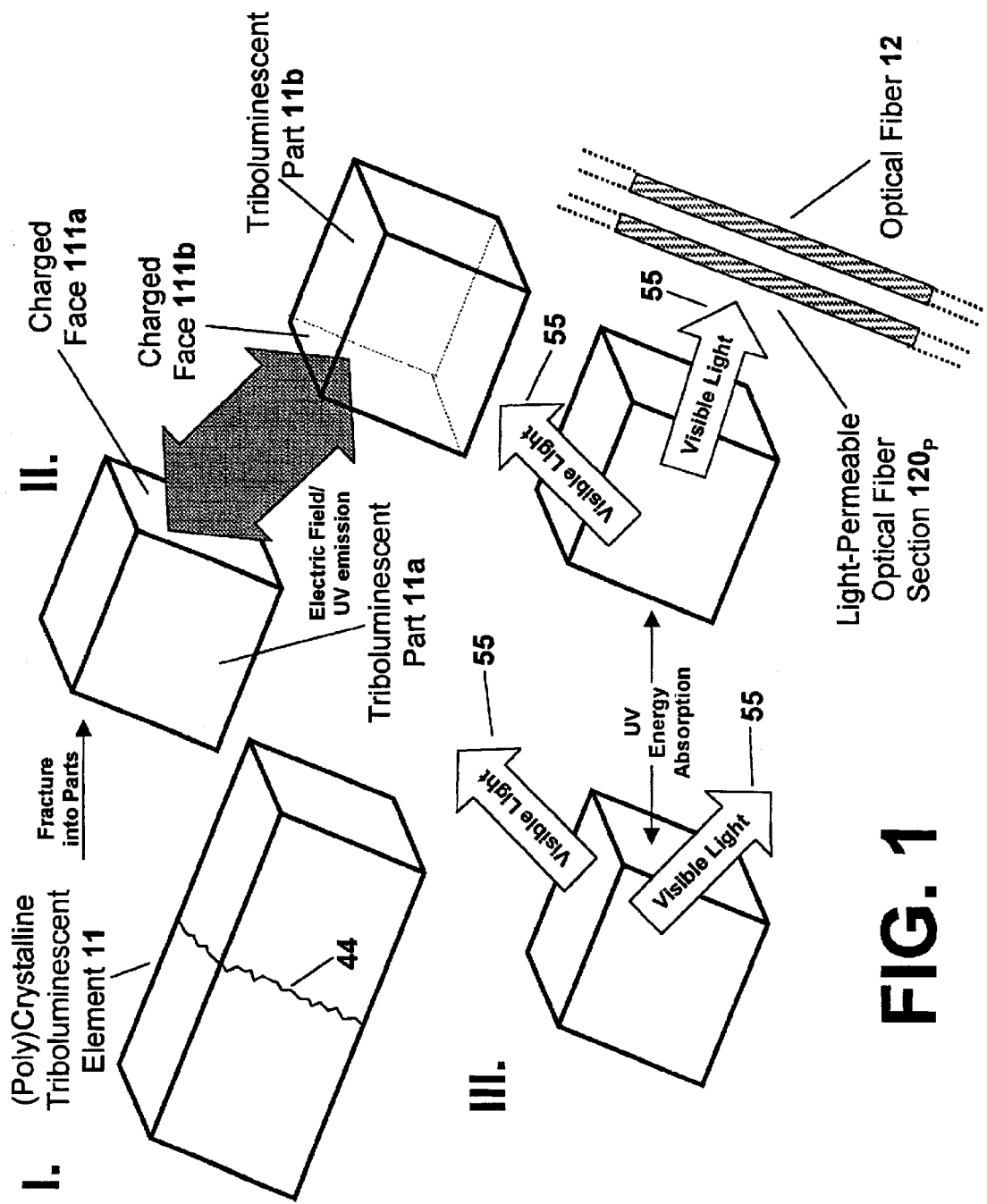
FIG. 1 is a schematic diagram illustrative of triboluminescence and its relationship to an optical fiber in accordance with typical practice of the present invention.

FIG. 1 summarizes the triboluminescent effect as related to typical practice of the present invention. Referring to FIG. 1, a crystal or polycrystal element 11 of triboluminescent material is fractured (indicated as stage "I"), and splits into triboluminescent element parts 11a and 11b (indicated as stage "II"), thereby creating charged faces 111a and 111b, respectively, of parts 11a and 11b. When energy is created between the two faces 111a and 111b, it is then reabsorbed into the triboluminescent material of parts 11a and 11b (indicated as stage "III"), which will then glow. It is this luminescent glow that appears when triboluminescent material is fractured.

Figure 2:
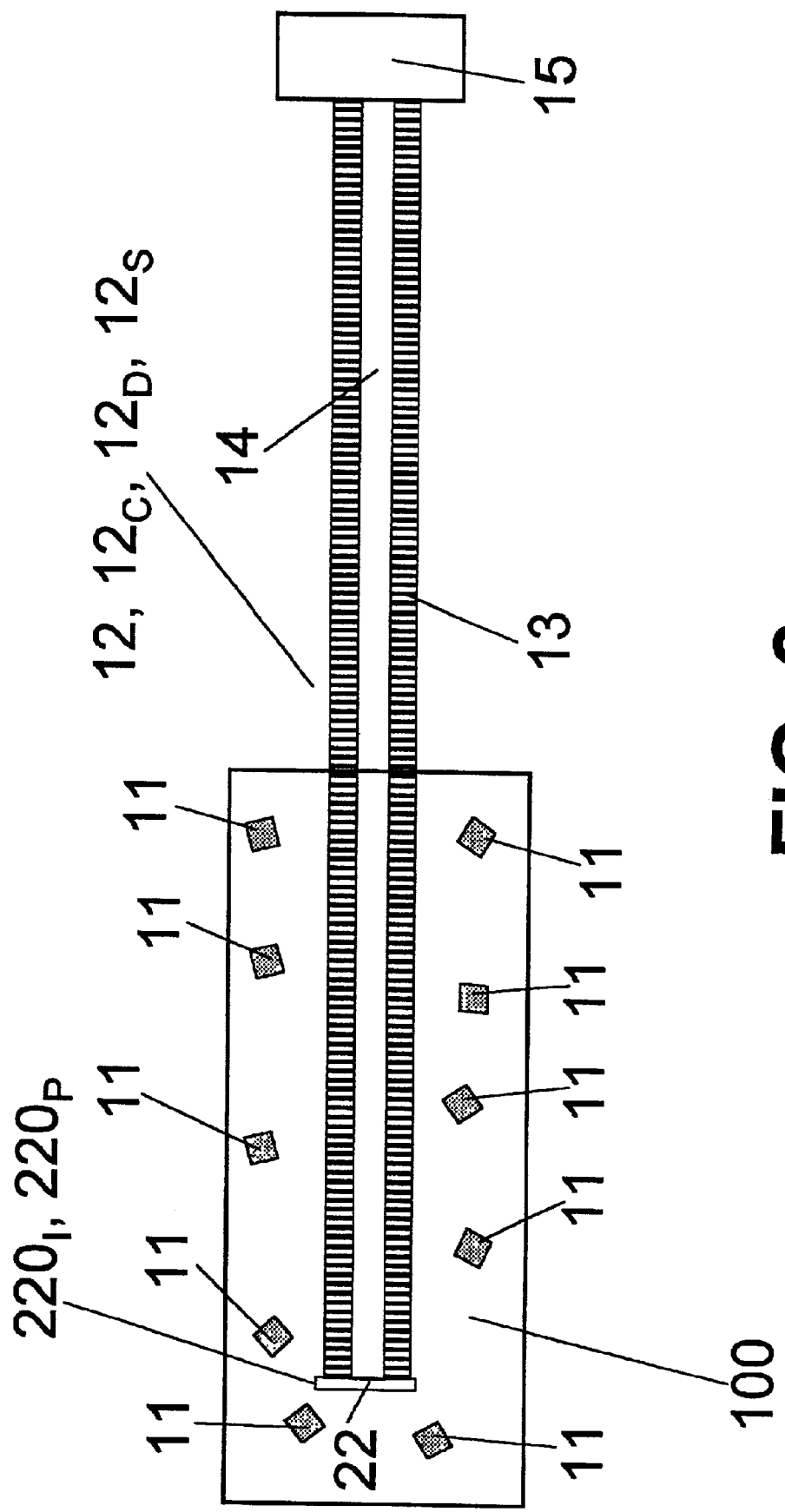
FIG. 2 is a diagrammatic plan view of an embodiment of damage sensing in accordance with the present invention, particularly showing a composite structure, the association with the composite structure of triboluminescent material elements and an optical fiber, and the connection of a photosensitive device with the optical fiber. The composite structure can be considered to be viewed either from above (wherein the optical fiber is coupled with the composite structure so as to be on a surface of the composite structure), or sectionally (wherein the optical fiber is coupled with the composite structure so as to be inside of or beneath the surface of the composite structure), or both from above and sectionally.

Reference is now made to FIG. 2, which describes the general setup and operation of a typical composite damage sensor in accordance with the present invention. A composite structure 100 is impregnated with triboluminescent crystals or polycrystals 11. The triboluminescent material 11 may be incorporated into the matrix (of a matrix composite), the reinforcement (of a matrix composite), the filler (of a matrix composite), or an interface (e.g., between two layers of a composite laminate), depending on the inventive application. This composite can be of any composition, including large choices of materials for the reinforcement/filler phase and the matrix phase.

Still with reference to FIG. 2 and again with reference to FIG. 1, the main prerequisite for the operation of the present invention's sensor is that light coming from the fracture of the triboluminescent crystals 11 (which have been incorporated into the composite 100) be able to be transmitted to the optical fiber 12. The optical fiber 12 is embedded into the composite 100 in any area of composite 100 where detection of mechanical damage is desired. Optical fiber 12 includes cladding 13 and fiber core 14. Upon the occurrence of damage to composite 100, the light resulting from such damage to composite 100 will be transmitted through optical fiber cladding 13 to optical fiber core 14, and/or will enter optical fiber core 14 from the end tip 22 of optical fiber 12. This light will then be transmitted to a photodetector 15, which will consequently indicate a light signal and, therefore, the coincidental mechanical damage to composite 100. In the present invention's fiber optic sensor system there is no traditional light source; the sensor is passive. The light is created within the composite structure 100 when (i) the composite structure 100 incurs damage and (ii) the triboluminescent material 11 present also (e.g., concomitantly) fractures, thereby causing a light signal to be absorbed (taken in) by and transmitted via optical fiber 12.

As shown generally in the figures, optical fiber 12 includes an outer covering (optical fiber cladding 13) and a light-transmittable inner core (optical fiber core 14). The present invention's optical fiber 12 can be constructed or configured in various ways, generally falling into two categorical "light-permeable" approaches, viz., "continuous" and "discrete." A continuous optical fiber $12_C$ has a cladding $13_P$ which is permeable (e.g., transparent or translucent) to light throughout (or nearly throughout) the entire length of optical fiber 12. A discrete optical fiber $12_D$ includes: (i) at least one light-permeable fiber optic section $120_P$ having a light-permeable cladding, section $130_P$; and, (ii) at least one light-impermeable fiber optic section $120_I$ having a light-impermeable cladding, section $130_I$. Thus, cladding 13 is permeable to light (e.g., transparent or translucent) in at least one section $120_P$ of optical fiber 12, and is impermeable to light (e.g., opaque) in at least one section $120_I$ of optical fiber 12. If there are two or more light-permeable optical fiber sections $120_P$ of a discrete optical fiber $12_D$, they will generally be unconnected (distinct) sections.

Figure 3:
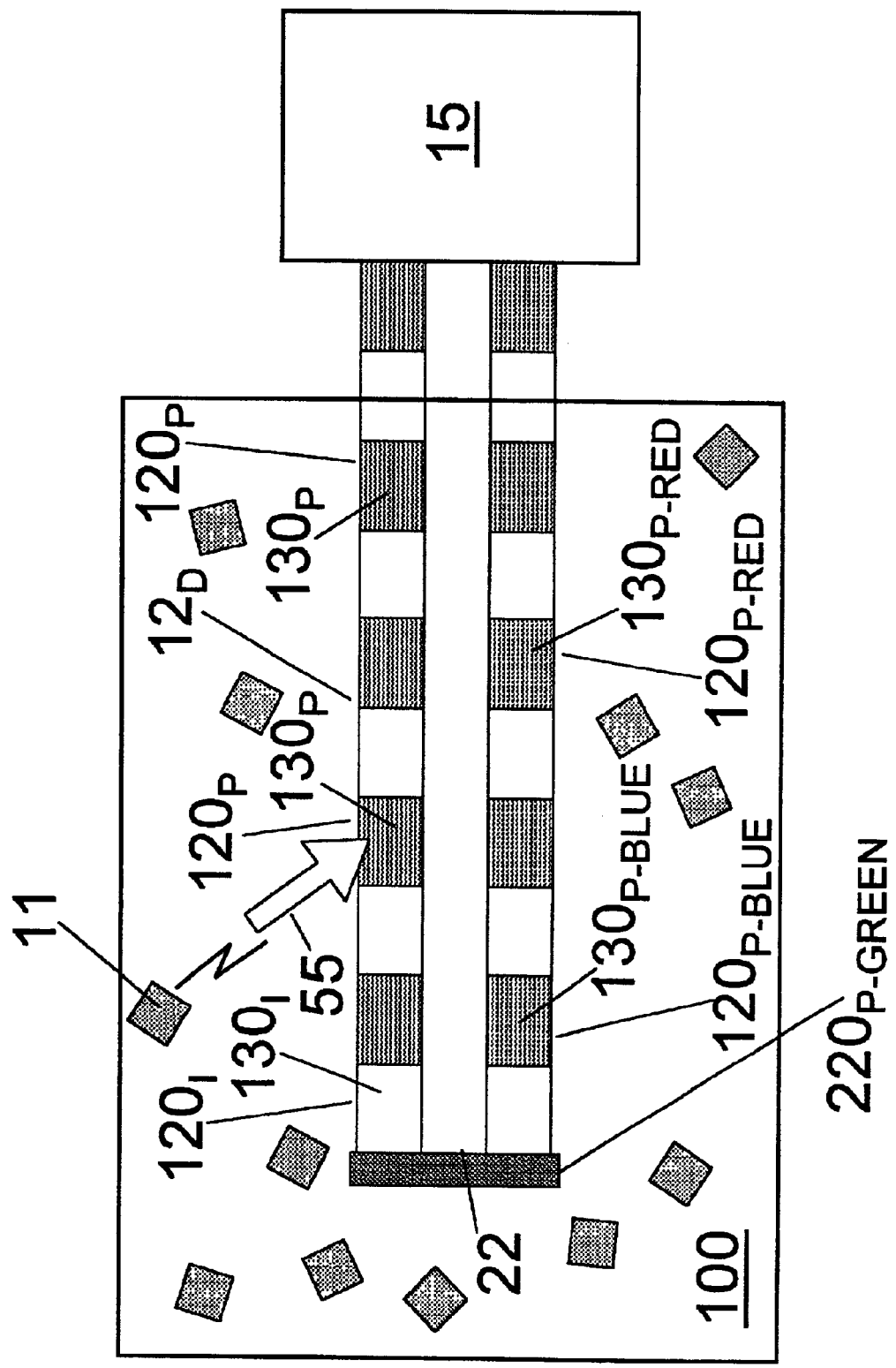
FIG. 3 is a diagrammatic plan view, similar to the view shown in FIG. 2 but slightly enlarged, of an inventive embodiment such as shown in FIG. 2, particularly illustrating the characteristic of light permeability of the exterior covering of the optical fiber intermittently along the length of the optical fiber.

Typically, the "sections" 120 of a discrete optical fiber $12_D$ are axially sequential segments (arranged side-to-side along the length of discrete optical fiber $12_D$), such as shown in FIG. 3; however, inventive practice of a discrete optical fiber $12_D$ can involve any configuration wherein at least one portion/section is a light-permeable section $120_P$ and at least one portion/section is a light-impermeable section $120_I$. For instance, such sections can be contradistinguished and contraposed as upper and lower sections of discrete optical fiber $12_D$, rather than as side-to-side sections of discrete optical fiber $12_D$, such as shown in FIG. 3. Usually, in side-to-side sectional configurations, if there are plural light-permeable optical fiber sections $120_P$, then at least two light-permeable optical fiber sections $120_P$ will be separated by light-impermeable optical fiber sections $120_I$. Generally in inventive practice, a "discrete" fiber optic approach is superior to a "continuous" fiber optic approach for purposes of more definitively determining the location or locations of detected damage to composite 100.

Hence, the optical fiber 12 used in typical inventive practice differs significantly from a standard optical fiber used in conventional practice. To further explain, in a standard optical fiber the outer layer (also referred to herein as the "cladding") of the optical fiber traps light to be channeled only in the core (i.e., the inner or central area) of the optical fiber. Essentially, the optical fiber cladding is opaque; light does not pass through the optical fiber cladding, but is only transmitted by the optical fiber core. The optical fiber cladding is characterized by a lower index of refraction, whereas the optical fiber core is characterized by a higher index of refraction.

In contrast, according to the present invention, light is taken in from outside the optical fiber 12 so as to pass through the optical fiber cladding 13 and into the optical fiber core 14, so that the light may be detected elsewhere (e.g., by means of electronic photodetection equipment). In order to accomplish this, a new kind of optical fiber—more specifically, a new kind of optical fiber cladding—is provided by the present invention. According to the present invention, at least a portion of the optical fiber cladding is effectively stripped away and replaced with a different, "alternative" cladding material, so that light may pass, from outside the optical fiber 12, through the cladding 13 and into the optical fiber core 14. The present invention's alternative cladding material is fight-permeable, e.g., transparent or translucent to light. Two inventive methodologies according to which this kind of light-permeability can be effectuated are illustrated in FIG. 3 and FIG. 4, which show, respectively, "discrete" fiber optic practice and "continuous" fiber optic practice.

Figure 4:
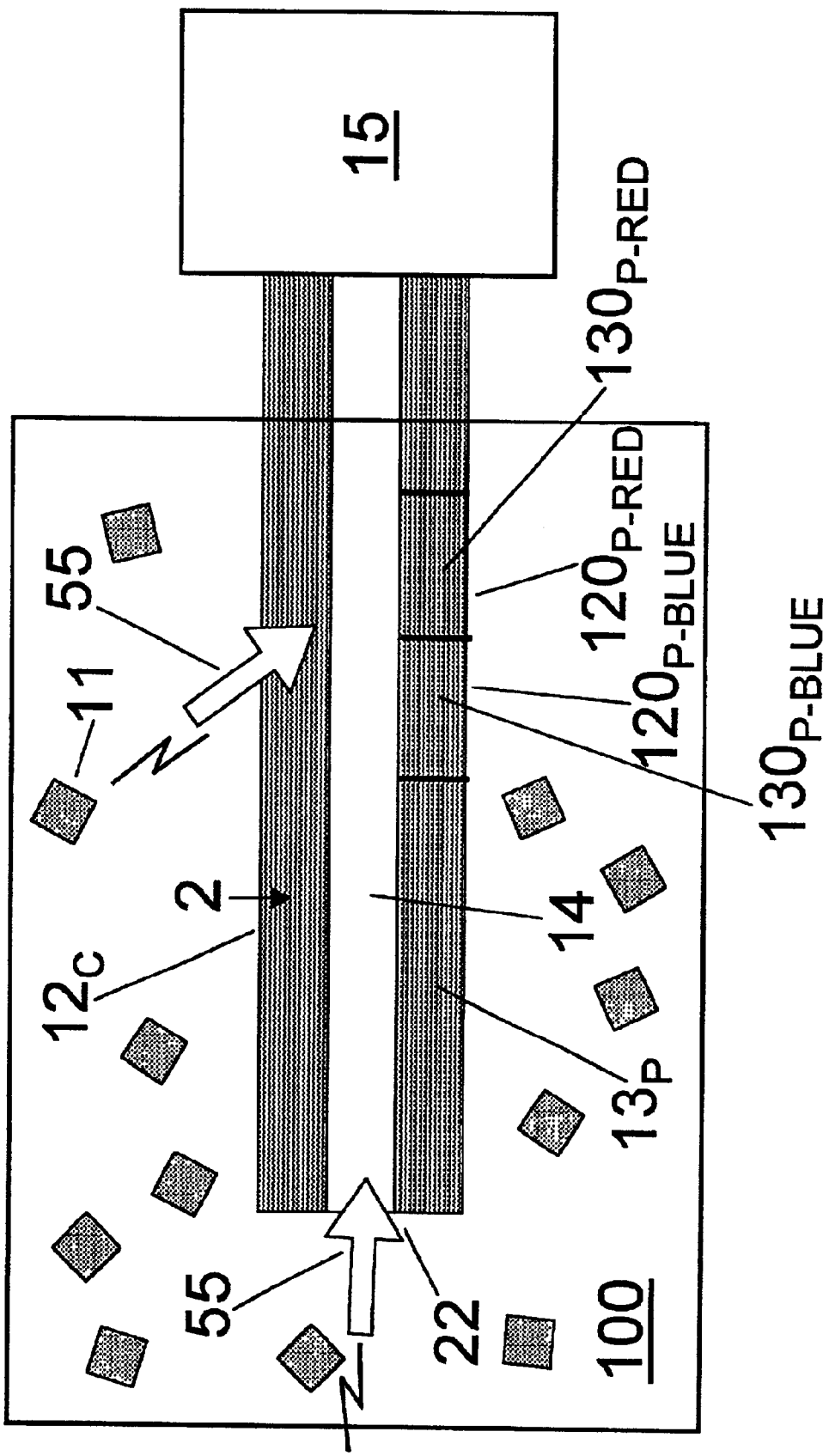
FIG. 4 is a diagrammatic plan view, similar to the view shown in FIG. 3, of an inventive embodiment such as shown in FIG. 2, particularly illustrating the characteristic of light permeability of the exterior covering of the optical fiber at least substantially continuously along at least substantially the entire length of the optical fiber.

As shown in FIG. 3 and FIG. 4 and other figures herein, composite 100 is rich in triboluminescent material, composite 100 having a multiplicity of triboluminescent elements 11 distributed therein. Discrete optical fiber $12_D$ and continuous optical fiber $10_C$ are shown in FIG. 3 and FIG. 4, respectively. With reference to FIG. 3 (and again with reference to FIG. 1), a crack 44 forms in composite 100, causing triboluminescent light emission 55. The light would normally be prevented from entering the fiber core by a standard cladding. However, according to the present invention, the installation of a special, light-permeable cladding $13_P$ in one or more certain segments (light-permeable fiber optic sections $120_P$) allows the light 55 to enter fiber core 14. This alternative cladding $13_P$ is transparent to the wavelength or wavelengths (at least one wavelength) of light coming from crack 44. The light 55 (or a portion thereof) which gains admission into optical fiber 12 via cladding $13_P$ is transmitted via core 14 to photodetector 15.

According to some inventive embodiments, the light-permeable cladding $13_P$ is attributed with a wavelength-determinative quality, such as by having a particular color, tint or hue. Thus, for instance, in addition to allowing propagation of the light 55 to the optical fiber core 14, alternative cladding $13_P$ could contain a photosensitive dye, thereby selectively changing the wavelength of the light 55 transmitted therethrough to the fiber core 14. In this manner, wavelength-determinative light-permeable cladding $13_P$ can inform the photodetector 15 as to which location along optical fiber 12 the light 55 entered. For example, wavelength-determinative light-permeable cladding section 130$_{P\text{-}RED}$, encompassed by optical fiber section 120$_{P\text{-}RED}$, can impart information that red light entered cladding section 130$_{P\text{-}RED}$, thereby suggesting that damage to structure 100 occurred in the vicinity of cladding section 130$_{P\text{-}RED}$. Similarly, wavelength-determinative cladding 130$_{P\text{-}BLUE}$, encompassed by optical fiber section 120$_{P\text{-}BLUE}$, can impart information that blue light entered cladding 130$_{P\text{-}BLUE}$, thereby suggesting that damage to structure 100 occurred in the vicinity thereof In fact, the present invention can be practiced so that a continuous optical fiber or a discrete optical fiber contains serial or contiguous wavelength-determinative sections, such as shown in FIG. 4, wherein wavelength-determinative red light-permeable cladding section 130$_{P\text{-}RED}$ and wavelength-determinative blue light-permeable cladding section 130$_{P\text{-}BLUE}$ are adjacent to each other.

Photodetector 15 is intended herein to be broadly representative of any of a variety of known electronic apparatus which may serve the purpose of somehow indicating the presence or existence of a degree of light which has originally radiated from triboluminescent material and which has arrived at or culminated in the electronic apparatus. Hence, terms such as "photodetector" or "photosensor" or "photosensitive device" are synonymously intended herein to generally refer to apparatus capable of identifying, registering, recording, representing, presenting a readout, signaling, digitizing, processing, displaying, etc., or some combination thereof in a manner indicative of the light received by the apparatus.

With reference to FIG. 4, in some inventive applications the location of crack 44 along the length of optical fiber 12 is not important. If, instead, cognizance is desired of simply the presence of a crack 44 anywhere in the composite 100, an arrangement such as depicted in FIG. 4 can be effected according to this invention. As shown in FIG. 4, the cladding 13 along the entire length of optical fiber 12 is light-permeable cladding 13$_P$. That is, cladding 13 is altered to accept the light 55 from the crack 44 in the composite 100, so that the light 55 proceeds into the fiber core 14 and is transmitted to the photodetector 15.

Sometimes a relatively small problem area—one which is deemed to be especially susceptible to a certain kind of damage, for example—is identified in a structure such as composite 100. Perhaps the inventive practitioner wishes merely to "keep an eye" specifically on this vulnerable location. For such objectives, inventive practice might suitably provide for implementation of a completely "standard" optical fiber 12$_S$ (i.e., an optical fiber having cladding 13$_I$, which is impermeable to light, throughout the length of the optical fiber). Optical fiber 12 shown in FIG. 2 is envisionable as either a standard optical fiber 12$_S$ or a discrete optical fiber 12$_D$ or a continuous optical fiber 12$_C$, each of which can be practiced according to the present invention. Let us assume, for example, that optical fiber 12 shown in FIG. 2 is a standard optical fiber 12$_S$; according to some inventive embodiments, standard optical fiber 12$_S$ can have an optical fiber tip 22 which can admit triboluminescently emitted light at a location of interest in composite 100. Inventive use of an optical fiber tip 22 can be made in addition to or as an alternative to inventive use of light-permeable cladding 13$_P$, regardless of whether such cladding 13$_P$ is in a discrete mode or a continuous mode. Moreover, a wavelength-determinative window-like optical fiber tip member (such as cap 220$_{P\text{-}GREEN}$ shown in FIG. 3), transparent only to a particular wavelength (e.g., green), can be provided at tip 22 of optical fiber 12. A light-permeable cap 220$_P$ or light-impermeable cap 220$_I$ can be coupled with (e.g., fitted on) an optical fiber 12 at its tip 22 whether it be a standard optical fiber 12$_S$, a discrete optical fiber 12$_D$ or a continuous optical fiber 12$_C$.

Figure 5:
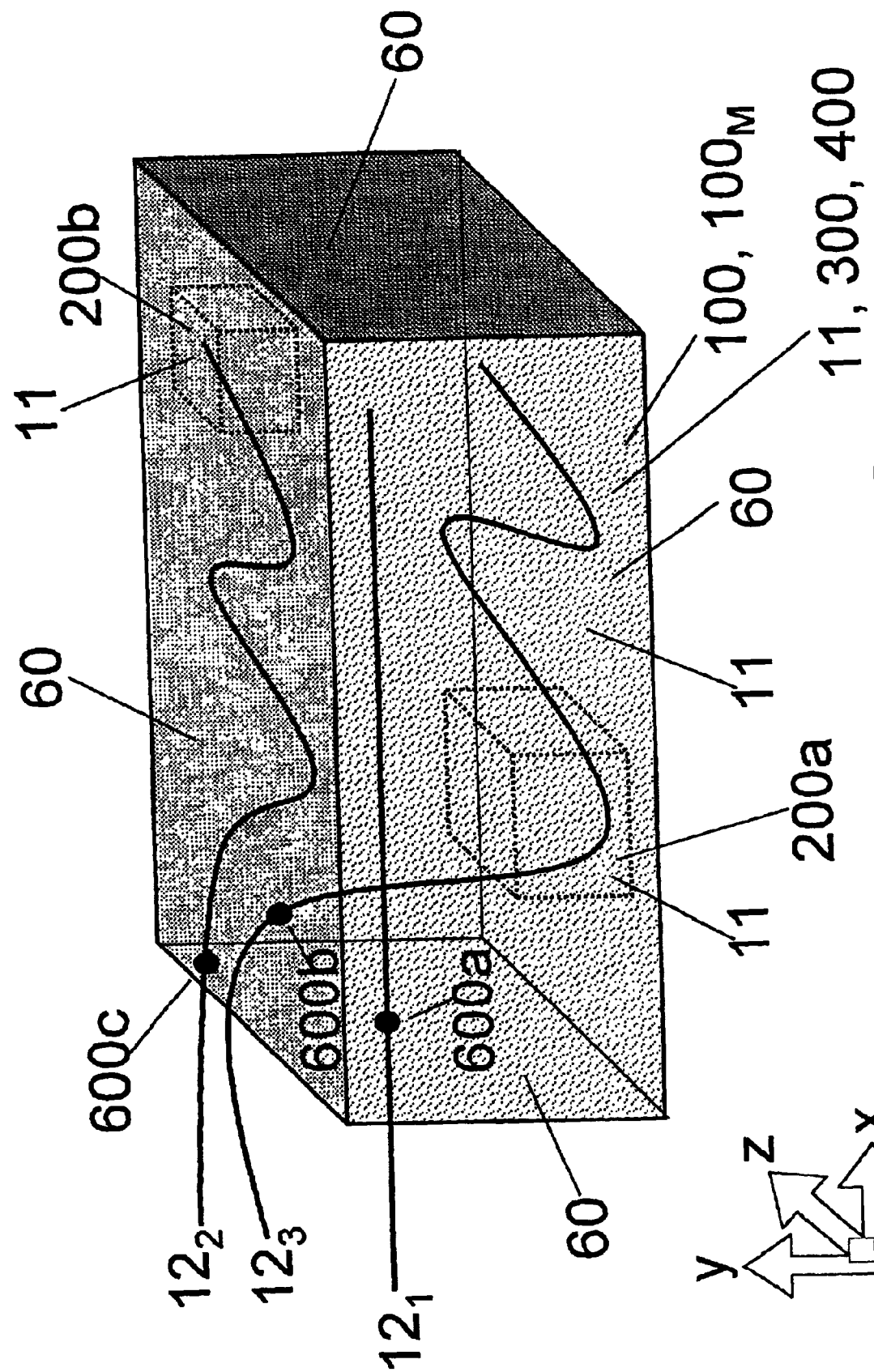
FIG. 5 is a diagrammatic perspective view of an embodiment of the present invention, particularly illustrating how a composite structure (shown, for exemplary purposes, to approximately describe a rectangular parallelepiped shape) can be infiltrated with triboluminescent elements and be coupled with optical fibers in various ways.

Using at least one optical fiber 12 as a sensing element in any of diverse inventive fashions such as described herein can permit maximum flexibility and versatility in detecting mechanical damage to any of diverse structures such as composite 100. With reference to FIG. 5, various configurations in monitoring a structure such as composite 10 for mechanical damage are possible in accordance with the present invention. The optical fiber 12 can be rectilinear and/or curvilinear, and can be disposed, relative to a structure such as composite 100, in any direction or directions in one, two or three dimensions.

As shown in FIG. 5, one-dimensional optical fiber 12$_1$ describes a straight line (shown in FIG. 5 for illustrative purposes as being disposed in a geometric x-y or x-z plane). Two-dimensional optical fiber 12$_2$ describes a curve which lies in a single geometric plane (shown in FIG. 5 for illustrative purposes as being disposed in an x-y or x-z plane). Three-dimensional optical fiber 12$_3$ describes a curve disposed in all three (x, y and z) directions in geometric space. As shown in FIG. 5, composite structure 100 has six side faces 60. Optical fiber 12$_1$ enters an end or side face 60 of composite 100 at point 600a and is run in a straight line through at least some of composite 100. Optical fiber 12$_2$ enters an end or side face 60 of composite 100 at point 600b and effectively "covers" an imaginary plane by varying direction within the plane in a sinusoidal pattern. Optical fiber 12$_3$ enters an end or side face 60 of composite 100 at point 600c and proceeds in a combination x-y-z direction; thus, by virtue of optical fiber 12$_3$ alone, composite 100 can be monitored for damage in all three directions in Cartesian space.

It is reemphasized that, although the one-dimensional optical fiber 12$_1$ mode and the two-dimensional optical fiber 12$_2$ mode are each shown as lying in a horizontal plane, inventive practice is limitless with regard to the locations, extents and orientations of such one and two-dimensional optical fiber modes and of three-dimensional optical fiber modes, as well. The limitlessness in these regards applies regardless of the nature of the structure 100 of interest, whether it be non-composite, laminar composite, matrix composite, or some combination thereof According to this invention, an optical fiber 12 can be oriented in any direction or directions, situated anywhere on and/or in a structure, and thus associated with the structure to any of greater or lesser extents of optical fiber 12. For instance, after entering a structure such as composite 10, optical fiber 12 can be threaded in any desired direction or pattern.

A noteworthy principle of inventive practice is the selective association, with the structure 10 of interest, of either the triboluminescent material 11 or the optical fiber(s) 12 or both the triboluminescent material 11 and the optical fiber(s) 12. As previously noted herein, a fiber optic tip 22 can be strategically positioned so as to pinpoint a specific spot on or in a structure 100. More generally, any fiber optic line such as optical fiber 12 can be strategically positioned for sensing damage at one or more particular locations. A fiber optic line 12 can be placed exteriorly (e.g., tangentially or superficially, such as upon or embedded at a surface of structure 100) with respect to the structure 100. Alternatively, a fiber optic line 12 can be placed interiorly with respect to structure 100. Alternatively, a fiber optic line 12 can be placed, at different locations along its length, both exteriorly and interiorly with respect to structure 100. The location or locations of light-permeable optical fiber cladding 13$_P$ and/or optical fiber tip 22 are especially important in these respects.

The locating of triboluminescent elements 11 can similarly serve strategical purposes pertaining to damage detection of structure 100. As shown in FIG. 5, composite structure 100 is shown to be a matrix composite structure 100$_M$ which is "globally" infiltrated with triboluminescent elements 11. However, depending on the inventive application, it may be unnecessary to distribute triboluminescent elements 11 in a global fashion, i.e., throughout matrix composite structure 100$_M$; hence, as portrayed by composite regions 200a and 200b, a composite structure can be regionally infiltrated with triboluminescent elements 11 (in one or more selected regions such as regions 200a and 200b), rather than globally infiltrated with triboluminescent elements 11. Moreover, triboluminescent elements 11 can be located at or near a surface area (such as a side or end face 60 shown in FIG. 5) of composite structure 100$_M$, and or more interiorly within composite structure 10$_M$.

Figure 6:
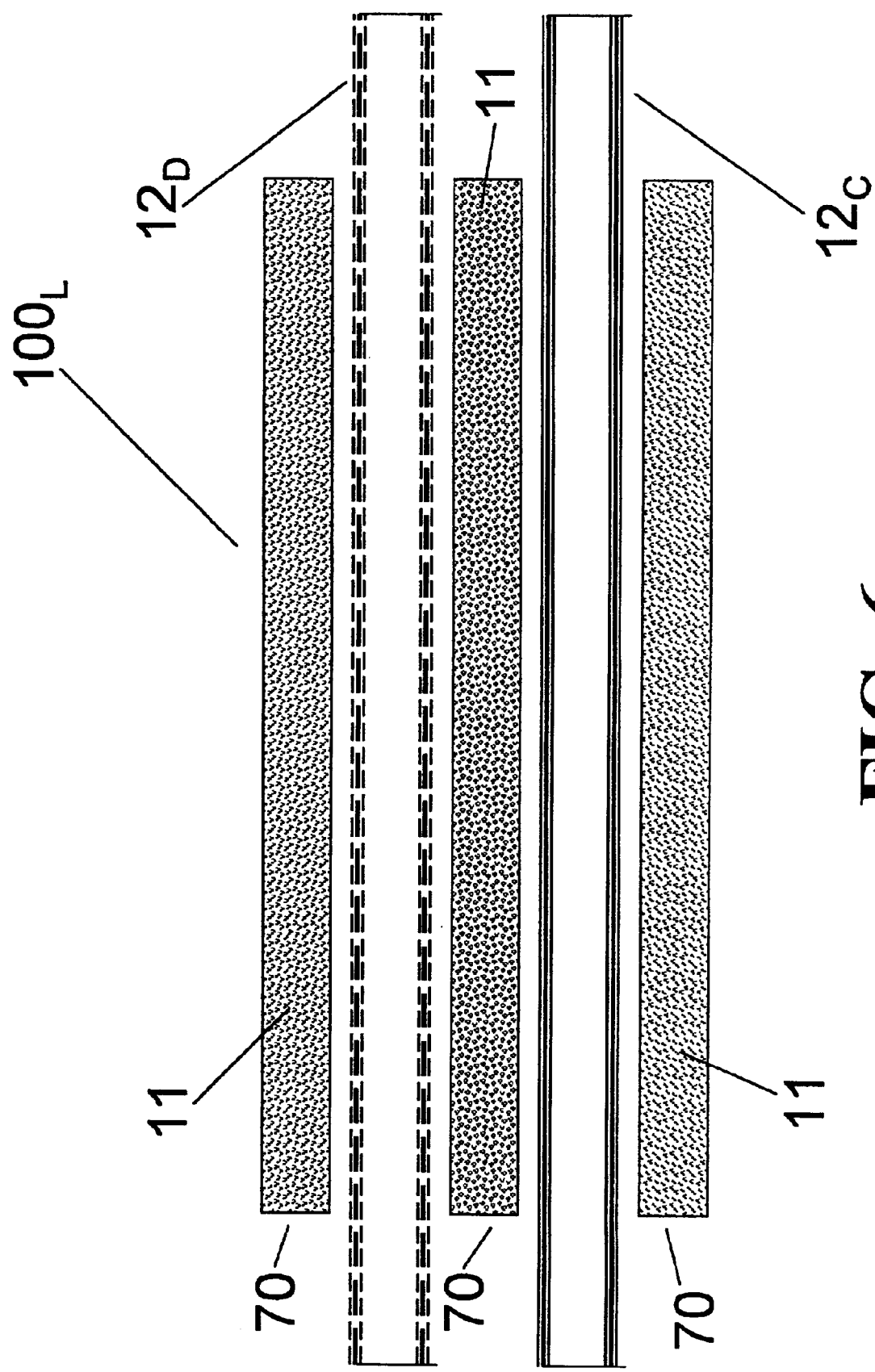
FIG. 6 is a partial elevation view of an embodiment of the present invention, particularly illustrating how a composite laminate structure (three lamina shown) can be infiltrated with triboluminescent elements and be coupled with optical fibers (two optical fibers shown in a longitudinal perspective) situated between the lamina.

In accordance with the present invention, a fiber optic line such as optical fiber 12 can be embedded in any composite 100, regardless of shape, size or type. Fiber optic line 12, for instance, can be incorporated with a fibrous reinforcement, or can be molded into a non-fibrous composite. Still referring to FIG. 5 and also referring to FIG. 6 through FIG. 9, various composite structures are fully or partially depicted. Two popular kinds of composite structures are matrix composites and laminar composites. As shown in FIG. 6 through FIG. 9, an optical fiber 12 can be placed intermediate two adjacent laminas 70, at least one of which is at least partially infiltrated with triboluminescent elements 11. FIG. 6 shows a continuous optical fiber 12$_C$ and a discrete optical fiber 12$_D$, each situated between two laminas (layers) 70 of laminar composite 100$_L$.

Figure 7:
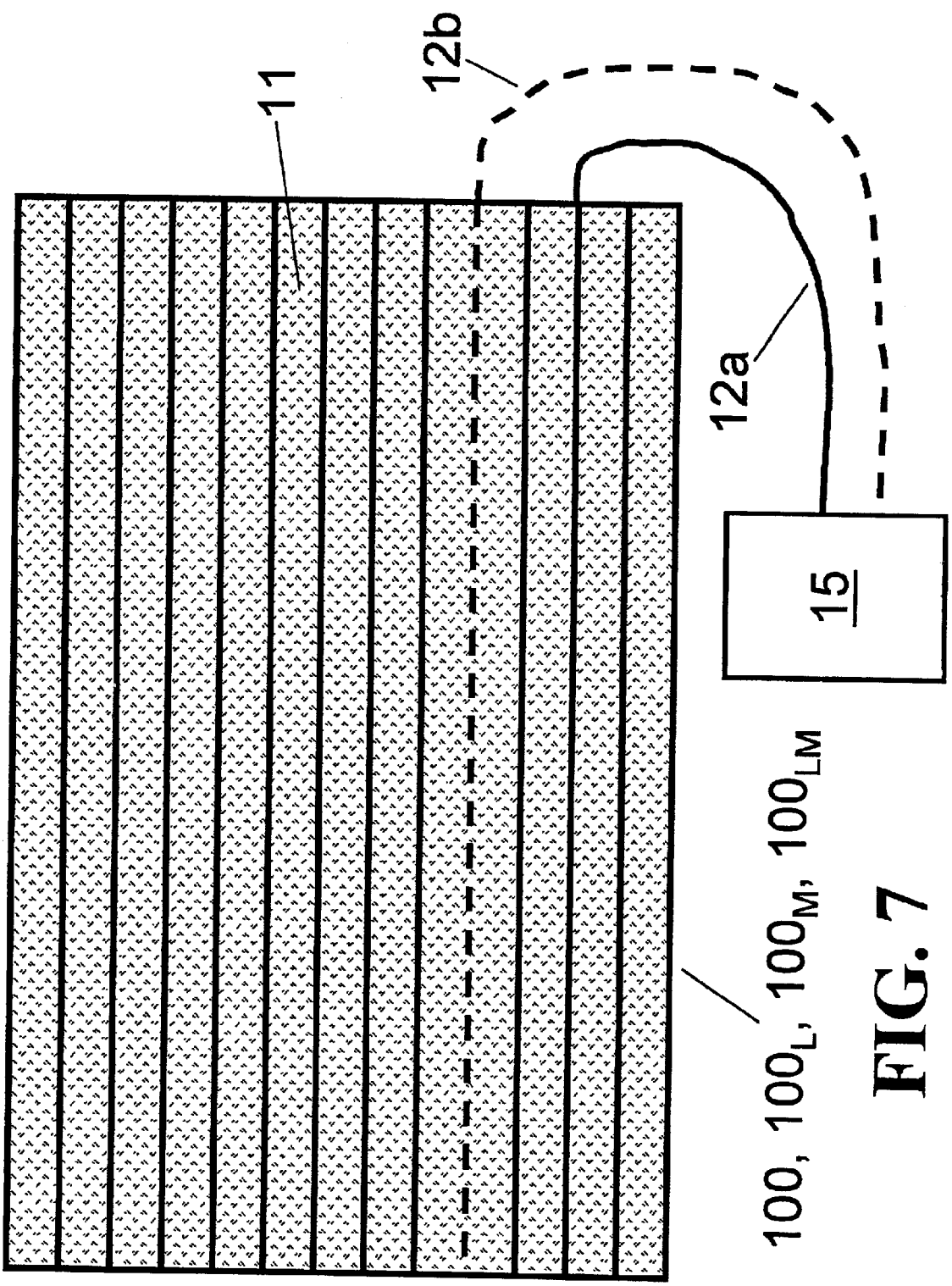
FIG. 7 is a diagrammatic plan view of an embodiment of damage sensing in accordance with the present invention, particularly showing a composite structure, the association with the composite structure of triboluminescent material elements and optical fibers, and the connection of a photosensitive device with the optical fibers. The composite structure can be considered to be viewed either from above (wherein the optical fibers are coupled with the composite structure so as to be on a surface of the composite structure), or sectionally (wherein the optical fiber is coupled with the composite structure so as to be inside of or beneath the surface of the composite structure), or both from above and sectionally.

According to some inventive embodiments, at least one lamina 70 can itself represent a matrix composite, having fiber or particle reinforcement/filler distributed therein. Shown in FIG. 9 is a sort of hybrid composite structure 100$_{LM}$ which has both laminar and matrix indicia. FIG. 9 shows two adjacent laminas 70 wherein optical fibers 12a are placed between laminas 70, while optical fibers 12b are placed inside a lamina 70. Each optical fiber 12b shown in FIG. 9 can be all or part of a fiber reinforcement 80 wherein the lamina 70 containing it represents a fiber-reinforced matrix composite 100$_M$, wherein fiber-reinforced matrix composite 100$_M$ will usually have one or more triboluminescent elements 11 distributed therein according to this invention. FIG. 7 can be considered to represent either a laminar composite 100$_L$ or a matrix composite 100$_M$ or a combination laminar-matrix composite 100$_{LM}$. By way of illustration, optical fiber 12a is shown to be situated interstructurally similarly as optical fiber 12a is situated in FIG. 9; optical fiber 12b is shown to be situated intrastructurally similarly as optical fiber 12b is situated in FIG. 9.

Reference now being made to FIG. 10a through FIG. 10d, crystal or polycrystal triboluminescent elements 11 can be associated with a matrix composite structure 100 in any of various ways. Matrix composite structure 100 includes a matrix (e.g., resinous) phase 300 and one or more constituent phases selected from among a particulate reinforcement phase 400$_{RP}$, a fibrous reinforcement phase 400$_{RF}$ and a particulate filler phase 400$_{FP}$. As shown in FIG. 10a, particle reinforcements 400$_{RP}$ do not contain any triboluminescent material 11; rather, the triboluminescent material 11 is, or is included in, particle fillers 400$_{FP}$ and/or matrix 300. FIG. 10b shows only particle reinforcements 400$_{RP}$ each of which is totally or partially made of triboluminescent material 11. As shown in FIG. 10c, both particle reinforcements 400$_{RP}$ and particle fillers 400$_{FP}$ contain triboluminescent material 11. Some particle fillers 400$_{FP}$ do not contain any triboluminescent material 11. Several particles 400$_P$ each represent a triboluminescent element 11 constituting triboluminescent material 11 in whole or in part.

FIG. 10d shows a veritable medley of possibilities for incorporating triboluminescent elements 11 into a matrix composite 100$_M$. Optical fiber 12 is or is made part of a reinforcement fiber 400a$_{RF}$, which lies adjacent to and in parallel with another reinforcement fiber 400b$_{RF}$ having a quantity of triboluminescent material, triboluminescent element 11, incorporated therein as a section or portion thereof. Also shown are triboluminescent elements 11 which are, or are part of, particle fillers 400$_{FP}$ and particle reinforcements 400$_{RP}$. Further shown are triboluminescent elements 11 which are incorporated into the matrix 300 material itself In accordance with the present invention, any and all of these and similar approaches to incorporation of triboluminescent material 11 are possible, whether practiced individually or combinationally in any manner. Practically any amount of triboluminescent material 11 and any number of fiber optic lines 12 may be used in accordance with the present invention.

Other embodiments of this invention will be apparent to those skilled in the art from a consideration of this specification or practice of the invention disclosed herein. Various omissions, modifications and changes to the principles described may be made by one skilled in the art without departing from the true scope and spirit of the invention which is indicated by the following claims.

What is claimed is:

1. A combination suitable for detecting damage in an object, said combination comprising fiber optic means and triboluminescent means each being adaptable to association with said object so that a mechanical event attendant said damage is capable of causing said triboluminescent means to emit light at least some of which is transmissible by said fiber optic means, wherein:

said fiber optic means includes outer casing means and inner transmissive means;

at least a portion of said outer casing means is capable of allowing at least some said emitted light to pass therethrough so as to reach said inner transmissive means; and said inner transmissive means is capable of transmitting at least some said emitted light which has passed through said outer casing means.

2. The combination according to claim 1, further comprising photosensitive means wherein, when at least some said emitted light is transmitted by said fiber optic means, said photosensitive means is capable of responding to said transmitted light so as to indicate the presence of at least some said transmitted light.

3. The combination according to claim 1, wherein:

said at least a portion of said outer casing means is at least two portions of said outer casing means; and each said portion of said outer casing means is capable of allowing at least some said emitted light of a particular wavelength to pass therethrough; and said particular wavelength differs for at least two said portions of said outer casing means.

4. A combination suitable for detecting damage in an object, said combination comprising fiber optic means and triboluminescent means each being adaptable to association with said object so that a mechanical event attendant said damage is capable of causing said triboluminescent means to emit light at least some of which is transmissible by said fiber optic means, wherein said fiber optic means includes open tips means, said open tip means being devoid of said outer casing means so as to allow at least some said emitted light to reach said inner transmissive means.

5. Damage-autosensitive apparatus comprising:

a structure;

at least one fiber optic line, each said fiber optic line being connectable to a photodetector and being situated so that a portion of said fiber optic line is in communication with said structure; and at least one triboluminescent element, each said triboluminescent element being integrated with said structure and being sufficiently proximate a said fiber optic line so that, upon an occurrence of damage to said structure:
 an accompanying mechanical action upon said triboluminescent element results in a luminescent emission of light by said triboluminescent element; and
 at least portion of said luminescently emitted light is transmissible to said photodetector via said fiber optic line;

wherein each said fiber optic line includes an outer coaxial fiber optic portion and an inner coaxial fiber optic portion;

wherein at least a section of each said fiber optic line portion communicating with said structure has a corresponding section of said outer coaxial fiber optic portion that is permeable to light; and wherein, as to each said light-permeable section of said outer coaxial fiber optic portion, upon a said occurrence of damage to said structure at least a portion of said luminescently emitted light permeates said light-permeable section so that at least a portion of said permeated luminescently emitted light is transmissible to said photodetector via said inner coaxial fiber optic portion.

6. Damage-autosensitive apparatus as recited in claim 5, wherein at least one said fiber optic line is situated so that a portion of said fiber optic line is in communication with an external portion of said structure.

7. Damage-autosensitive apparatus as recited in claim 5, wherein at least one fiber optic line is situated so that a portion of said fiber optic line is in communication with an internal portion of said structure.

8. Damage-autosensitive apparatus as recited in claim 5, wherein:

said structure is an overall structure including a laminar composite structure having plural lamina; and at least one said fiber optic line is situated so that a portion of said fiber optic line is positioned between two adjacent said lamina.

9. Damage-autosensitive apparatus as recited in claim 5, wherein:

said structure is an overall structure including a fiber-reinforced matrix composite structure having a matrix phase and plural fiber reinforcements situated in said matrix phase; and at least one said fiber optic line is situated so that a portion of said fiber optic line is positioned within said matrix phase so as to function as a said fiber reinforcement.

10. Damage-autosensitive apparatus as recited in claim 5, wherein:

said structure is an overall structure including a matrix composite structure having a matrix phase and plural constituents situated in said matrix phase;

each said constituent is selected from the group consisting of fiber reinforcement, particle reinforcement and particle filler; and at least some said triboluminescent elements are integrated with said matrix composite structure whereby each said triboluminescent element constitutes at least a part of a said constituent.

11. Damage-autosensitive apparatus comprising:

a structure;

at least one fiber optic line, each said fiber optic line being connectable to a photodetector and being situated so that a portion of said fiber optic line is in communication with said structure; and at least one triboluminescent element, each said triboluminescent element being integrated with said structure and being sufficiently proximate a said fiber optic line so that, upon an occurrence of damage to said structure:
 an accompanying mechanical action upon said triboluminescent element results in a luminescent emission of light by said triboluminescent element; and
 at least a portion of said luminescently emitted light is transmissible to said photodetector via said fiber optic line;

wherein at least a section of each said fiber optic line portion communicating with said structure is permeable to light;

wherein at least a portion of said luminescently emitted light permeates at least one said light-permeable section so that at least a portion of said permeated luminescently emitted light is transmissible to said photodetector;

wherein at least two sections of each said fiber optic line portion communicating with said structure are permeable to light; and wherein each said light-permeable section is permeable to light characterized by a different wavelength.

12. Damage-autosensitive apparatus as recited in claim 11, wherein at least one fiber optic line is situated so that a portion of said fiber optic line is at least one of the following:

in communication with an external portion of said structure;

in communication with an internal portion of said stricture; and in communication with both an external portion and an internal portion of said structure.

13. Damage-autosensitive apparatus as recited in claim 11, wherein said triboluminescent elements are integrated with said structure so that at least one of the following sets of conditions obtains:

(a) at least one said fiber optic line is situated so that a portion of said fiber optic line is in communication with an external portion of said structure, and at least some said triboluminescent elements are sufficiently proximate said fiber optic portion communicating with said external structure portion;

(b) at least one said fiber optic line is situated so that a portion of said fiber optic line is in communication with an internal portion of said structure, and at least some said triboluminescent elements are sufficiently proximate said fiber optic portion communicating with said internal structure portion; and (c) at least one said fiber optic line is situated so that a first portion of said fiber optic line is in communication with an external portion of said structure and so that a second portion of said fiber optic line is in communication with an internal portion of said structure, at least some said triboluminescent elements are sufficiently proximate said first fiber optic portion communicating with said external structure portion, and at least some said triboluminescent elements are sufficiently proximate said second fiber optic portion communicating with said internal structure portion.

14. Damage-autosensitive apparatus as recited in claim 11, wherein each said light-permeable section is one of:

a longitudinal section of the corresponding said fiber optic line portion; and an end section of the corresponding said fiber optic line portion.

15. Damage-autosensitive apparatus as recited in claim 11, wherein said photodetector is producible of an indication of at least a portion of said transmitted permeated luminescently emitted light.

16. Damage-autosensitive apparatus comprising:

a structure;

a photodetector;

at least one fiber optic line, each said fiber optic line being connected to said photodetector and being situated so that a portion of said fiber optic line is in communication with said structure, each said fiber line including an outer coaxial fiber optic portion and an inner coaxial fiber optic portion, said outer coaxial fiber optic portion including at least one light-permeable section, said light-permeable section being permeable to light so that light reaches said inner coaxial fiber optic portion; and at least one triboluminescent element, each said triboluminescent element being integrated with said structure and being sufficiently proximate a said fiber optic line so that, upon an occurrence of damage to said structure:

an accompanying mechanical action upon said triboluminescent element results in a luminescent emission of light by said triboluminescent element; and at least a portion of said luminescently emitted light permeates at least one said light-permeable section so that at least a portion of said permeable luminescently emitted light is transmitted to said photodetector via said inner coaxial fiber optic portion; and as to each said light-permeated light-permeable section said photodetector produces an indication of at least a portion of said transmitted permeated luminescently emitted light.

17. A method of sensing the damage condition of an object, said method comprising:

integrating triboluminescent material with said object;

providing at least one fiber optic line; and associating each said fiber optic line with said object and with a photosensitive device so that, following a damage-causing event accompanied by a mechanical action upon at least some said integrated triboluminescent material;

a first quantity of a resultant triboluminescent light emanation is admitted by said fiber optic line; and a second quantity of said resultant triboluminescent light emanation is transmitted by said fiber optic line to said photosensitive device, said second quantity being included in said first quantity;

wherein each said fiber optic line has an exterior membrane and an interior light-transmissive path; and wherein each said exterior membrane is at least partially light-admissible along at least a portion of the length of the corresponding said fiber optic line, said fiber optic line thereby being admissible of said first quantity of said resultant triboluminescent light.

18. A method as defied in claim 17, wherein at least one of the following obtains:

said integrating triboluminescent material with said object includes selecting at least one location at which said object is susceptible to damage; and said associating of said at least one fiber optic line with said photosensitive device includes selecting at least one location at which said object is susceptible to damage.

19. A method of sensing the damage condition of an object, said method comprising:

integrating triboluminescent material with said object;

providing at least one fiber optic line; and associating at least one fiber optic line with said object and with a photosensitive device so that, following a damage-causing event accompanied by a mechanical action upon a least some said integrated triboluminescent material, a quantity of resultant triboluminescent light emanation is transmitted by said at least one fiber optic line to said photosensitive device;

wherein said at least one fiber optic line includes at least two fiber optic line portions which are at least partially light-admissible;

wherein each said fiber optic line portion is admissible only to light of a corresponding wavelength; and wherein at least two said corresponding wavelengths are different.

* * * * *